United States Patent
Welch et al.

(10) Patent No.: US 10,342,646 B2
(45) Date of Patent: Jul. 9, 2019

(54) METHOD OF, AND SYSTEM FOR SMOOTHING TEETH

(71) Applicants: James D. Welch, Omaha, NE (US); Janet M. Wehrli, Omaha, NE (US)

(72) Inventors: James D. Welch, Omaha, NE (US); Janet M. Wehrli, Omaha, NE (US)

(*) Notice: Subject to any disclaimer, the term of this patent is extended or adjusted under 35 U.S.C. 154(b) by 48 days.

(21) Appl. No.: 15/731,373

(22) Filed: Jun. 7, 2017

(65) Prior Publication Data

US 2017/0296312 A1 Oct. 19, 2017

Related U.S. Application Data

(63) Continuation-in-part of application No. 14/756,809, filed on Oct. 17, 2015, now Pat. No. 9,833,386.

(60) Provisional application No. 62/392,809, filed on Jun. 13, 2016, provisional application No. 62/496,321, filed on Oct. 13, 2016.

(51) Int. Cl.
| | |
|---|---|
| *A61C 5/20* | (2017.01) |
| *A61C 17/16* | (2006.01) |
| *A61K 6/027* | (2006.01) |
| *A61C 3/00* | (2006.01) |
| *A61C 17/00* | (2006.01) |
| *A61C 13/20* | (2006.01) |
| *A61C 8/00* | (2006.01) |
| *A61K 6/00* | (2006.01) |
| *A61K 6/06* | (2006.01) |

(52) U.S. Cl.
CPC .............. *A61C 13/206* (2013.01); *A61C 5/20* (2017.02); *A61C 8/008* (2013.01); *A61C 17/16* (2013.01); *A61K 6/0017* (2013.01); *A61K 6/0047* (2013.01); *A61K 6/027* (2013.01); *A61K 6/0668* (2013.01); *A61C 3/00* (2013.01); *A61C 17/00* (2013.01)

(58) Field of Classification Search
CPC ......... A61C 17/00; A61C 17/16; A61C 17/22; A61C 13/206; A61C 5/20; A61C 8/008; A61C 3/00; A61C 3/025; A61K 6/0668; A61K 6/027; A61K 6/087; A61K 6/0017; A61K 6/0047; A61K 33/06
USPC .................................................. 433/215, 216
See application file for complete search history.

(56) References Cited

U.S. PATENT DOCUMENTS

| | | |
|---|---|---|
| 2,358,730 A | 9/1944 | Nelson et al. |
| 4,148,872 A | 4/1979 | Wagenknecht et al. |
| (Continued) | | |

OTHER PUBLICATIONS

G.C. America, Mi Paste.

*Primary Examiner* — Wade Miles
*Assistant Examiner* — Drew S Folgmann
(74) *Attorney, Agent, or Firm* — James D. Welch

(57) ABSTRACT

A method of smoothing teeth by, for instance, filling in cracks, chips and eroded areas by applying calcium and/or casein and/or phosphate and a source of OH⁻ ions thereto. The method optionally provides that very thin layer(s) of dental cement be interlaced with other applied materials, and that the results be maintained in contact with the teeth involved by application of a composition of matter that adheres to said teeth and holds the results in place, while allowing at least some permeation of saliva therethrough. The method can optionally involve application of a backing strip or tray or the like to secure the other materials in place, but this is not a requirement where the composition of matter is sufficiently securing.

5 Claims, 4 Drawing Sheets

SMOOTHER

(56) References Cited

U.S. PATENT DOCUMENTS

| | | | |
|---|---|---|---|
| 4,150,112 A | 4/1979 | Wagenknecht et al. |
| 4,156,715 A | 5/1979 | Wagenknecht et al. |
| 4,159,315 A | 6/1979 | Wagenknecht et al. |
| 4,161,517 A | 6/1979 | Wagenknecht et al. |
| 4,225,579 A | 9/1980 | Kleinberg |
| 4,229,485 A | 10/1980 | Brown et al. |
| 4,397,837 A | 8/1983 | Raaf |
| H83 H | 7/1986 | Poletto et al. |
| 5,249,570 A | 10/1993 | Cox |
| 5,405,836 A | 4/1995 | Richar et al. |
| 5,455,024 A | 10/1995 | Winston et al. |
| 5,693,334 A | 12/1997 | Miskewitz |
| 5,944,510 A | 8/1999 | Greiner et al. |
| 5,993,786 A | 11/1999 | Chow et al. |
| 6,014,950 A | 1/2000 | Rogers |
| 6,050,224 A | 4/2000 | Owens |
| 6,309,676 B1 | 10/2001 | Lewandowski |
| 6,322,772 B1 | 11/2001 | Wehrli |
| 6,405,081 B1 | 6/2002 | Ward |
| 6,441,354 B1 | 8/2002 | Seghatol et al. |
| 6,475,471 B1 | 11/2002 | Wehrli |
| 6,509,007 B2 | 1/2003 | Rajaiah et al. |
| 6,596,298 B2 * | 7/2003 | Leung .................. A23G 3/50 424/435 |
| 6,610,276 B2 | 8/2003 | Melman |
| 6,649,147 B1 | 11/2003 | Ye et al. |
| 6,669,928 B1 | 12/2003 | Gurol |
| 6,685,971 B2 | 2/2004 | Xu |
| 6,827,041 B2 | 12/2004 | Hague |
| 6,886,497 B1 | 5/2005 | Hague et al. |
| 6,905,673 B2 | 6/2005 | Rajaiah et al. |
| 6,997,708 B2 | 2/2006 | Allred et al. |
| 7,013,838 B2 | 3/2006 | Hague |
| 7,022,314 B2 | 4/2006 | Barabolak et al. |
| 7,029,690 B1 | 4/2006 | Wehrli |
| 7,955,591 B1 | 6/2011 | Wehrli |
| 8,658,139 B1 | 2/2014 | Cutler |
| 2003/0113271 A1 | 6/2003 | Rajaiah |
| 2003/0124230 A1 | 7/2003 | Zielinski |
| 2003/0175326 A1 | 9/2003 | Thombre |
| 2003/0206948 A1 | 11/2003 | Gergely et al. |
| 2004/0057910 A1 | 3/2004 | Lee |
| 2004/0101493 A1 | 5/2004 | Scott et al. |
| 2004/0101494 A1 | 5/2004 | Scott et al. |
| 2004/0110111 A1 | 6/2004 | Wasylucha |
| 2004/0118360 A1 | 6/2004 | Hague et al. |
| 2004/0224472 A1 | 9/2004 | Jia |
| 2005/0008584 A1 | 1/2005 | Montgomery et al. |
| 2005/0019275 A1 * | 1/2005 | Sagel .................. A61K 8/0208 424/53 |
| 2005/0071927 A1 | 4/2005 | Hague et al. |
| 2006/0088482 A1 | 4/2006 | Wulknitz et al. |
| 2006/0153935 A1 | 7/2006 | Blahut |
| 2007/0298003 A1 | 12/2007 | Chandra |
| 2010/0150974 A1 * | 6/2010 | Butler .................. A61K 8/24 424/401 |
| 2010/0203478 A1 * | 8/2010 | Rubbert .............. A61C 5/007 433/212.1 |
| 2012/0012030 A1 | 1/2012 | Saghir et al. |

* cited by examiner

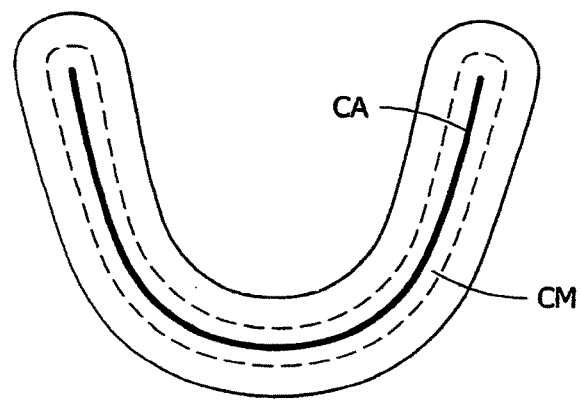
Fig. 7
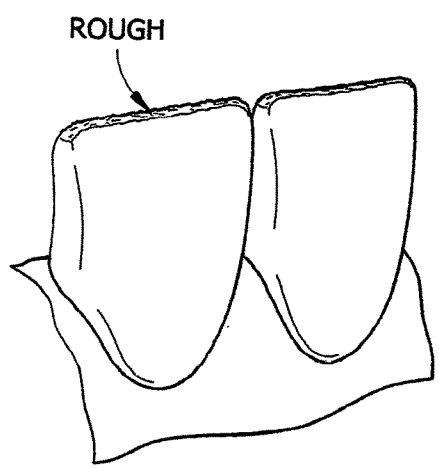 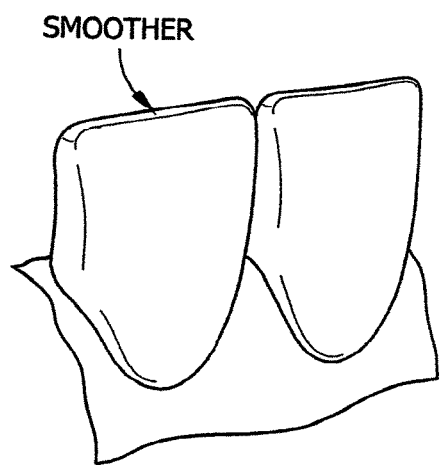
Fig. 8a          Fig. 8b

METHOD OF, AND SYSTEM FOR SMOOTHING TEETH

This application is a CIP of application Ser. No. 14/756,809 Filed Oct. 17, 2015 and Claims Benefit of Provisional Application Ser. Nos. 62/392,809 Filed Jun. 13, 2016 and 62/496,321 Filed Oct. 13, 2016.

TECHNICAL AREA

The present invention relates to repair of teeth, and more particularly to method of smoothing teeth by, for instance, filling in cracks, chips and eroded areas by applying calcium and/or casein and/or phosphate, (eg. calcium phosphate), and a source of $OH^-$ ions thereto. The method optionally provides that very thin layer(s) of dental cement can be interlaced with other applied materials, and that the results be maintained in contact with the teeth involved by application of a composition of matter that adheres to said teeth and holds the results in place, while allowing at least some permeation of saliva therethrough. The method can involve application of a backing strip or tray or the like to secure the other materials in place, but this is not a requirement where the adherent composition of matter is sufficiently securing.

BACKGROUND

Inventor Welch has been acting as Patent Attorney for Co-inventor and Client, Janet M. Wehrli, in Patent efforts regarding oral treatments for many years. The latest of said inventions being subject in U.S. Pat. No. 9,498,414, which relates to means for controlling plaque on teeth, and more particularly to a method involving application of a composition of material to teeth and gums. The basic step in the 414 Patent involves applying a composition of matter to teeth which:
  adheres to teeth and serves as a barrier between teeth and gums, and the environment;
  inhibits plaque from adhering to teeth; and optionally dissolves and/or absorbs plaque.
Said composition of matter further serves to neutralize acids and freshen breath.

Attorney Welch has, over the years, experimented with various dental maintenance matters personally and has developed some novel approaches thereto, some of which are disclosed herein. One such approach, for instance, being the use of tooth adhesive and an orthodontic band to secure over 30 years of use from a molar that cracked down the middle. In keeping with his researcher orientation, he recently conceived and practiced the invention disclosed herein to the end of achieving a very unexpected result. Co-Inventor Wehrli has expressed great surprise at what she has observed regarding the Upper edges of his Lower Frontal teeth. Attorney Welch mentioned to her that he had been practicing a method that had resulted in said "edges" becoming far "smoother" than they had been when he ran his tongue thereover. That is, they seem to have been recalcified. Co-Inventor Wehrli has a long background in the oral care industry, and upon observing Attorney Welch's teeth, expressed that what she saw was not expected. There was definite evidence of what appears to be renewed calcification, (eg. remineralization of enamel). As Attorney Welch has included a composition of matter that Co-Inventor Wehrli developed in his research, she is included as Co-Inventor in this effort.

A Computer Search of Patents provided:

Replacement Sheet a) Using Recalcify Teeth and beeswax . . . no hits;
b) Using Recalcify Teeth and Sodium Bicarbonate . . . one hit:
    Patent to Wehrli U.S. Pat. No. 7,955,591.
Further, a Patent to Cuther, U.S. Pat. No. 8,658,139 is mentioned as it describes preventing tooth decay using Calcium Carbonate having a particle size of 1-100 nanometers.

And, a Patent to Seghatol et al., U.S. Pat. No. 6,441,354 is mentioned as it provides insight that known approaches to improving teeth are use of prosthetics, filling dental caries and application of caps.

Sensodyne Pro-Enamel™ is disclosed as it advertises that it's use can strengthen and re-harden enamel. Said product contains Potassium Nitrate and Sodium Fluoride.

It is also mentioned that a product named . . . "MI" Paste . . . is milk calcium based, (it is described as being derived from Milk Caesin and is identified as Casein Phosphopeptide—Amorphous Calcium Phosphate in the manufacturer's materials), and is used by Dental practitioners to encourage recalcification of teeth. (Full ingredients are: Butyl p-hydroxybenzoate, Casein phosphopeptides and amorphous calcium phosphate, D-sorbitol, Ethyl-p-Propylene, Flavoring, Glycerol, Guar Gum, Magnesium Oxide, Propyl p-hydroxybenzoate, Propylene Glycol, Phosphoric Acid, Silicon Dioxide, Sodium carboxymethyl cellulose, Sodium saccharide, Titanium dioxide, Water, Xyilitol, and Zinc oxide). Application is described by the providers of MI Paste™ as preferably via Prophy Cups and Custom Trays, and those skilled in its usage also sometimes use a burnishing procedure after it's application. The providers of MI Paste mention application by other than trays is possible, but nothing in their instructions suggest application of a composition of matter after application of MI Paste™ to teeth, of a composition of matter designed to secure and keep the MI Paste™ in contact with said teeth for a prolonged period of time, while also allowing at least some access of saliva to the interface between said teeth and MI Paste™. The providers of MI Paste™ point out that said Paste adheres to biofilms, plaque, bacteria, hydroxyapatite and soft tissue and that localizes availability of calcium and phosphate, (in this regard it is beneficial to clean teeth before it's use) It is noted that the present invention provides that perhaps, but not necessarily, phosphate can be present in a combined form as calcium phosphate. The providers of MI Paste™ also mention that those allergic to milk or hydrobenzoates should not use MI Paste™.

Additionally, as mentioned, MI Paste is derived from Milk Casein. It is disclosed that Powdered Casein is also available, such as that provided by Bodytech, under the name Micellar Casein, Slow Release. The manufacturer provides that said Powdered Casein contains Alanine, Arginine, Aspartic Acid, Cystein, Histadine, Isolucine, Leucine, Lysine, Methionine, Phenylanine, Proline, Serine, Threonine, Theonine, Tryptophan, Tryosine and Valine and a small amount of Potassium.

Another product is marketed under the Tradename Oraparx, and comprises approximately ⅛ edible adhesive, ⅝ oil and ⅖ plaque inhibiting material. This product provides $OH^-$ ions when in contact with saliva. See recent U.S. Pat. No. 9,498,414 to Wehrli for details. It was by use of this product that Inventor Welch discovered the methodology in this Application.

Another commercially available product marketed for use with teeth is called Lightform Band Cement. It is typically applied to secure braces in place, and adheres to teeth well. Lightform Band Cement is a two part epoxy-like product that when mixed and subjected to UV electromagnetic radiation, hardens. Even without application of UV electromagnetic radiation, given a sufficient much longer time however, the Lightform Band Cement hardens. Herein the Lightform Band cement and other materials with similar properties are referred to as dental cement. Dental Cements are generally classified, based on matrix, as:
  Phosphate (zinc phosphate, silico phosphate);
  Polycarboxylate (zinc polycarboxylate, glass isomer);
  Phenolate (zinc oxide-eugenol and EBA);
  Resin (polymeric).
ISO classifications are:
  Water-based acid-base cements: Zinc phosphate ($Zn_3(PO_4)_2$), Zinc Polyacrylate (Polycarboxylate), glass Ionomer (GIC) which contain metal oxide or silicate fillers embedded in a salt matrix.
  Non-aqueous/oil bases acid-base cements: Zinc Oxide Eugenol and Non-Eugenol Zinc Oxide which contain metal oxide fillers embedded in a metal salt matrix.
  Resin-based: Acrylate or Methacrylate resin cements, including the latest generation of self-adhesive resin cements that contain silicate or other types of fillers in an organic resin matrix.
Further, Dental Resin Cements are often formulated from dimethacrylates and polymethacrylates as well as methacrylates.

A bonding mechanism of resins can be an acid-base link to calcium in hydroxyapatite in dentin, similar to a resin-cement modified glass without the need of a glass isomere component.

It is further noted that many Dental Cements involve the use of independent etching, or self-etching, and that the typical use of Dental Cement is to fill microgaps between a tooth and a restorative material and assist in the retention of restorative material. Most use of Dental Cement is not as a restorative material per se., where restorative material refers to such as Crowns, Laminates, Inlays or Outlays. Conventional use of Dental Cements does not contemplate that it become a component of a restoration by combining very thin layers thereof with Calcium or Calcium+Phosphate or Casein Protein or the like.

Dental cements are disclosed in this Application as possibly beneficial to the present invention but their use is not preferred.

Further, it is disclosed that Dental Wax is available for use primarily for those who wear Braces, and use thereof to maintain contact of calcium powder etc. with teeth is disclosed.

Also, in addition to U.S. Pat. No. 9,498,414, also disclosed are Patents to Inventor Wehrli:
  U.S. Pat. Nos. 7,955,591; 7,029,690; 6,475,471 and 6,322,772.

In prosecution of Parent application Ser. No. 14/756,809, the Examiner cited:
  U.S. Pat. No. 4,397,837 to Raaf et al.;
  Published Application US 2003/0113276 by Rajaiah et al; and
  Published Application US 2004/0057910 by Lee et al.
in fashioning a Section 103 rejection. In view thereof, it is noted that the 837 Patent to Raaf et al. is based on the . . . sequential . . . application of two phases of materials, each containing different ingredients, namely, in either order of application, 1) water soluble calcium and 2) water soluble phosphate. There is no indication what-so-ever that only one phase should be applied, directly followed by application of an adherent material which serves to maintain contact of the contents of said one phase with teeth for a prolonged period of time. Rather, the two phases are applied sequentially so that ions in each are caused to be successively absorbed into dental enamel with the result that rehardening of demineralized areas in dental enamel are rehardened. See Col. 2, Lined 28-38 in Raaf et al. 837. As the present invention does not allow such a two phase approach, Raaf et al. 837 is avoided, again, because it requires the sequential application of two (2) phases, 1) one containing calcium and 2) one containing phosphate.

Further, there is no indication that any adherent material is applied to cause the two applied phase ingredients to remain in contact with teeth. In fact, no mention of adherent material is found in Raaf et al 837. The Examiner sought to overcome this deficiency in Raaf et al. 837 by citing a Published Application by Rajaiha et al. No. US2003/0113276. The 276 Rajaiha et al. reference, however, . . . requires . . . use of a Strip to maintain contact of a composition applied to teeth. The present invention does not require such an approach. Rajaiha et al. 276 is avoided if no strip is required.

Lee et al. Published Application No. US2004/0057910 mentions use of Beeswax. The Examiner cited Lee et al. 910, but this disclosure in Lee et al. 910 is not remotely, on its own, obviating of the present invention. And, as disclosed above, the Examiner's Raaf et al. 837 and Rajaiah et al. 276 references were avoided and not available to contribute to the disclosure in Lee et al. 910.

In additional Action by the Examiner in the Parent 809 Application, the Examiner cited as a Primary Reference a Published Application by Butler et al. No. 2010/0150974 which describes application of calcium and phosphate and whitening agent. The two "gels" therein both contain active ingredients, (Calcium and Phosphate respectively). Nothing in Butler et al. 974 suggests eliminating Phosphate in the second "gel" and replacing it with an edible adherent material, (eg. wax). Both the Butler et al. 974 "gels" contain active, but different materials, (ie. either calcium or phosphate). The invention in Butler et al. 974 would not work if the second "gel" did not contain an active ingredient, (complimentary to the first ingredient), but instead consisted of an edible adherent material! Further, "whitening agents" are included in the listing of negative limitations in this Application, and, along with other negative limitation which can be entered to Claims, based on avoidance of literature that uses an alternative to the approach disclosed by Applicants in this effort. Nothing therein suggests removing either component and a careful consideration of Butler et al. 974, shows that it does not at all disclose application of a second composition of matter consisting of combined edible adherent material (eg. wax), perhaps including and oil and plaque inhibiting material, (eg. sodium or potassium bicarbonate). The second composition in the Butler et al. 974 reference contains a source of phosphate ions, which is avoided by use of "consisting of" language, or by reciting phosphate or whitening agents as excluded from being required That is, nothing in Butler et al. 974 suggests eliminating phosphate in a second instance, and replacing it with edible adherent material (eg. wax). The invention in Butler et al. 974 would not work if that were done! The edible adherent material, (eg. wax), would not interact with calcium as does phosphate! Butler et al. 974 cannot then be held to anticipate or obviate the Present Invention, as any attempt to structure Butler et al. 974 to substitute edible adherent material, (eg.

wax), for phosphate would render the Butler et al. 974 invention unworkable! That is, Butler et al. 974 cannot be read to teach what would render the invention therein inoperable! Butler et al. 974 must then, be held only to teach away from Present Invention. In view of the foregoing one skilled in the art therefore would not be guided Butler et al. 974 to remove phosphate and replace it with edible adherent material! (It is noted that Butler et al 974 allows for reversing the order of application of calcium and phosphate, hence, the foregoing should be interpreted to also include the case where phosphate is applied first, and the edible adherent material is substituted for calcium).

Under Graham vs. John Deere, there must be something in a Primary Reference that would lead the Examiner to seek out additional references. In that light, Applicant's ask . . . what in Butler et al. 974 led the Examiner to seek out the Patent to Wehrli, U.S. Pat. No. 7,955,591; and the Published Applications by Blahut 2006/0153935, Lee et al., No. 2004/0057910 Raiaiah et al., No. 2003/0113276, Chandra 2007/0298003, Scott 2004/0101493? Applicant feels the Examiner simply noted that his Primary Reference by Butler et al. 974 was deficient in some respects, and looked for additional references that somehow mentioned things that are somehow relevant to said deficiencies, and then, without instructions being present in Butler et al. 974 as how to proceed, simply identified the mentioning of the things that are somehow relevant to said deficiencies, and declared Anticipation or Obviousness. How could one skilled in the art possibly have identified the additional references without using the Present Application as a Teaching Reference, and then what is more, proceed to ignore the many many many things therein that are irrelevant, identify the things that seem somehow relevant, modify them so as to arrive at exactly what is lacking in Butler et al. 974?

This is similar to the argument previously submitted to the end that there was nothing what-so-ever in Raaf 837 and Rajaiah 910 that would lead the Examiner to seek out Lee 276 to provide a source of Beeswax, other than a reading of the Present Application, which teaches the Examiner that Beeswax would be in any way desirable in Present Invention. In the present case the Examiner admits that Butler et al., 974 does not teach use of Beeswax (Page 13, Line 1 of his recent Action). Without something in Raaf 837 and Rajaiah 910 and now Butler et al. 974 to guide the Examiner to seek out Lee 276, it is apparent that the Examiner is using prohibited hindsight. An Examiner cannot read an Application, then perform an Examination based on cataloging all the required elements, finding references that mention somehow similar elements, in altered forms, and than just decree that because all the components have been known before, that it would be obvious to identify them, modify them as necessary and combine them so as to arrive at a New Invention . . . unless one of the References cited provides . . . instructions . . . to the Examiner as how to identify and modify and assemble the various modified components into the New Invention.

It is also noted that Lee et al. 910 requires use of a substrate (ie. a backing strip), and use of whitening agents.

Blahut 935 does mention use of coral calcium, but ONLY as a dentifrice. It is not applied to teeth to cause smoothing thereof. In fact, use of coral calcium as described in Blahut 935 would serve to roughen teeth, as does any application of abrasion thereto.

Rajaiah et al. 276 and Wehrli 591 both require use of backing strips, or equivalents, such as trays. Neither describes use of an edible adherent material.

Scott et al. 493 describes use of a chewable solid, and has the same drawback as does Blahut 935 in that abrasion is applied to teeth during practice of the invention. Again, that serves to remove material from teeth and roughen them. The present invention gently deposits material onto teeth and smooths them!

The present invention does not altogether require that use of Phosphate is prohibited . . . only that if it is used, it has to be present simultaneous with Calcium. It is possible that additional references might teach such simultaneous application of calcium and phosphate containing compositions, (eg. MI Paste is a Tradename product that provides such a combination), however, Applicant knows of no such reference which then fairly obviates that directly after applying such a combination of calcium and phosphate containing composition, the applying of an adherent composition, such as one comprising Beeswax, to maintain the calcium and phosphate in contact with teeth.

Another Published Patent Application, No. US2012/0012030 by Saghiri et al., is also cited as it describes a cement composition made up of nanoparticles of dicalcium and tricalcium silicate, bismuth oxide, gypsum, zeolite and stronium salt.

It is noted that Attorney/Applicant Welch attests that practice of the Invention as Claimed in Parent application Ser. No. 14/756,809 has provided a smoothing of the upper and lower edges on his lower and upper front teeth, respectively, said roughness having accumulated over his 70+ years. Continuing research has led to additional insight, which is found in Parent Provisional 62/496,321 filed on Oct. 13, 2016. Said additional insights are subject in this Application.

Need remains for methodology and supporting systems that when practiced cause a smoothing of teeth.

DISCLOSURE OF THE INVENTION

The present invention is a method of smoothing teeth consisting of the steps:

a) providing at least one tooth that is to be smoothed; practicing steps b) and c), or b) and c) and d) sequentially in the order as listed, or simultaneously via first mixing the components in steps b) and c), or b) and c) and d), respectively, and then practicing said combined steps as a single step;

b) applying a calcium powder or calcium containing composition of matter to an area on said at least one tooth that is to be smoothed;

c) applying a composition of matter that, when contacted by saliva provides OH⁻ ions to said area on said at least one tooth that is to be smoothed, over said calcium powder or calcium containing composition;

d) applying a composition of matter that adheres to teeth and serves as a barrier between teeth and gums and oral environment to said area of said at least one tooth that has had a calcium powder or calcium containing composition and the composition of matter that, when contacted by saliva provides OH⁻ ions, said composition, of matter serving to retain said calcium powder or calcium containing composition and the composition of matter that, when contacted by saliva provides OH⁻ ions, in place without requiring use of a backing strip;

d) maintaining the result of practicing steps a)-c) for at least one hour; and e) repeating at least steps b)-d).

Said method can involve, prior to step b) or after step c), the application of dental cement layer to a depth of less than a millimeter.

Said method can involve that said calcium powder or calcium containing composition comprises, in addition to calcium, phosphate, independently or as calcium phosphate; and/or wherein casein, which comprises at least one amino acid, is also applied, in mixture with said calcium powder or calcium containing composition, or sequential thereto so that both calcium and casein are present prior to step c) on said area on said at least one tooth that is to be smoothed.

(Note, the phosphate can be present as Calcium Phosphate).

Said method can involve that the composition of matter that, when contacted by saliva provides OH⁻ ions, consists of a selection from the group consisting of:
  sodium bicarbonate; and
  potassium bicarbonate.

Said method can provide that said calcium or calcium containing composition of matter, and said composition of matter that when contacted by saliva provides OH⁻ ions, are secured within a "U" shaped element.

Said method can provide that said calcium powder or calcium containing composition and said composition of matter that, when contacted by saliva provides OH⁻ ions are mixed together, and wherein said mixture is contained in, along with said composition of matter that adheres to teeth and serves as a barrier between teeth and gums and oral environment, are applied from a single container which provides separate access to said mixture of:
  said calcium powder or calcium containing composition and said composition of matter that when contacted by saliva provides OH⁻ ions, and
  said composition of matter that adheres to teeth and serves as a barrier between teeth and gums and oral environment.

The method can be alternatively recited as a method of smoothing teeth comprising the steps:
  a) providing at least one tooth that is to be smoothed;
  a') making a selection from the group consisting of:
  practicing b) and b') and b'') sequentially;
  first mixing the components in b) and b'), and then practicing b and b') simultaneously, followed by b''); and
  first mixing the components in b) and b') and b''), and then practicing b) and b') and b'') simultaneously as a single step;
wherein b), b') and b'') are:
  b) applying a calcium powder or calcium containing composition to an area on said at least one tooth that is to be smoothed;
  b') applying a composition of matter that, when contacted by saliva provides OH ions to said area on said at least one tooth that is to be smoothed;
  b'') applying an edible was containing composition of matter that adheres to teeth and serves as a barrier between teeth and gums and oral environment to said area of said at least one tooth, said composition of matter serving to retain present calcium powder or calcium containing composition and present composition of matter that, when contacted by saliva provides OH ions in place without requiring use of a backing strip, said composition of matter not requiring the presence of phosphate.

Said method further comprising:
  a'') maintaining the result of practicing steps a) and a') for at least one hour; and
  a''') repeating at least steps a) and a').

An alternative recitation of a present invention method of smoothing teeth comprises the steps of:
  a) providing an area of at least one tooth to be smoothed;
  b) applying a composition of matter to said at least one tooth comprising a selection from the group consisting of:
    b1) a mixture of 50% calcium powder and 50% sodium or potassium bicarbonate, by volume or equivalent by weight;
    b2) a mixture of at least 50% calcium powder and at least 25% sodium or potassium bicarbonate and up to 25% casein that comprises at least one amino acid, all by volume or equivalent by weight;
    b4) a mixture of at least 5096 calcium phosphate and at least 25% sodium or potassium bicarbonate, up to 25% casein that comprises at least one amino acid, all by volume or equivalent by weight;
  c) maintaining the scenario of achieved in step b) for at least a few minutes; and
  d) repeating steps b) and c).

A more generalized present invention method of smoothing teeth comprises the steps of:
  a) providing an area of at least one tooth to be smoothed;
  b) applying to said area of said at least one tooth, a composition of matter that comprises at least one selection from the group consisting of:
    b1) dental cement layer to a depth of less than a millimeter; and
    b2) a composition of matter that serves as a barrier between teeth and gums and oral environment;
  and at least one selection from the group consisting of:
    b3) a composition of matter that, when contacted by saliva provides OH⁻ ions;
    b4) a composition of matter that comprises bio-available calcium and optional phosphate containing composition of matter;
    b5) a powdered casein containing composition of matter; and
    b6) a powdered calcium containing composition of matter;
in an order that encourages the at least one selection from the group b3), b4), b5) and b6) to be retained by the at least one selection from the group consisting of b1) and b2) in contact with said area of said at least one tooth to be smoothed;
  c) maintaining the scenario of at least two selections achieved in step b) for at least half an hour; and
  d) repeating steps b) and c).

(It is noted that in Step b1), the use of a depth of Dental Cement is limited to less than a millimeter. In practice the preferred depth is far less that a millimeter, and is applied only to aid with adherence of subsequently applied Calcium or Casein etc. The purpose of the Dental Cement is to become a part of a restorative material which is sequentially deposited in many very thin layers rather than to attach a separate Restorative material such as a Crown or Laminate etc. to a tooth. As such, it has been found that applying more than a very minimal layer depth leads to the Dental Cement quickly coming back out of small imperfections in a tooth. In practice it has been found that application of a Dental cement by rubbing a region of a tooth to be smoothed with a finger that has a very small amount of said Dental Cement applied thereto many times back and forth leads to an appropriate very thin layer thereof being applied that improves adherence to subsequently applied Calcium, or Calcium+Phosphate, or Protein Casein etc., which Dental Cement does not then immediately come back out, but rather becomes a part of a very thin layer of Restorative Material comprising a mixture of said Dental cement and said Calcium, or Calcium+Phosphate, or Protein Casein etc.).

Said method can involve that step b) involves selection of the b2) dental cement layer to a depth of less than a millimeter, and wherein said dental cement layer is applied in at least one order selected from the group consisting of:
  a') before at least one selection from b3)-b6); and
  b') after at least one selection from b3)-b6).

The method can be characterized in that no intervening steps are present between application of at least one selection from b1) and b2), and application of at least one selection from the group of b1), b2) b3) and b4), where the selection from b1) and b2) can precede and/or follow application of selection(s) from b1), b2) b3) and b4). That is, for instance, any selection(s) from b1), b2) b3) and b4) can be applied together followed directly by application of at least one selection from b1) and b2); or b1) can be applied followed directly by application of at least one selection from the group of b1), b2) b3) and b4), followed directly by application of at least one selection from b1) and b2). This is to distinguish over the cited U.S. Pat. No. 4,397,837 to Raaf et al. which requires sequential application of calcium containing composition and phosphate containing composition so that ions of each enter teeth sequentially. The preferred approach of the present invention is that when two or more selections from b1), b2) b3) and b4) are used, that they be mixed together and then applied simultaneously. However, this does not prevent, for instance, a selection from b5) and/or b6), and/or a b4) mixture of calcium and phosphate from being applied before b3), followed directly by application of b2).

Any recited present invention methodology can involve repeating it based on a selection from the group consisting of:
  at last once a day;
  at least twice a day;
  at least three times a day;
  at least four times a day;

Any present invention methodology can involve that the at least one tooth is from a selection form the group consisting of:
  cat teeth;
  dog teeth; and
  human teeth.

Said method can involve that the at least one tooth is present in the mouth of a human, and the optional step a) of surface cleaning said at least one tooth is practiced and involves surface cleaning said at least one tooth by:
  a1) swishing hydrogen peroxide around in the mouth human's mouth for at least one minute before spitting it out;
  a2) preparing a toothbrush by moistening it with ethyl alcohol, followed by applying triple antibiotic ointment*, (⅛ inch diameter), thereto, followed by dipping said toothbrush into Epsom Salts, followed by dipping said toothbrush into sodium bicarbonate and optionally adding a dab, (about ¼ inch in diameter), of toothpaste*, then brushing said surface area of at least one tooth with said so prepared toothbrush;
  a3) before spitting the results of practicing step a2) out, swishing said results of practicing step a2) around in said human mouth for at least 15 minutes;
  a4) spitting out the remaining results of practicing step a3) out.

(*Triple antibiotic ointment comprises 500 units of Bacitracin, Neomycin sulfate equivalent of 3.5 mg of neomycin base, and Polymycin B as 10,000 units of Polymyxin B sulfate; and a preferred toothpaste is Sensodyne Tarter Control which has active ingredients of Potassium Nitrate and Sodium Fluoride and inactive ingredients of hydrated silica, sorbitol, glycerin, pentasodium triphosphate, PEG-8, flavor, titanium dioxide, cocamidopropyl betain, sodium methyl, cocoyl taurate, xanthan gum, sodium hydroxide, sodium saccharin and sucralose).

Said method can involve that the b3) composition of matter, provides OH⁻ ions when contacted by saliva;
  adheres to teeth and serves as a barrier between teeth and gums, and the environment;
  inhibits plaque from adhering to teeth; and
  optionally dissolves and/or absorbs plaque.
wherein said method comprises selecting at least one of b5) and b6), and wherein b2) and b3) are selected and mixed together to form a composition of matter that is applied to aide with securing said b5) and/or b6) in place.

Said method can provide that b1), b2) b3), b4), b5) and b6) are selected, and said method comprises:
  a') applying a b1) layer of dental cement to a depth of less than one millimeter;
  b') applying b3), b4), b5) and b6), as selected from the group consisting of:
    a mixture of b3), b5) and b6);
    a mixture of b3), b4) and b5);
    a mixture of b3) and b4);
  c') applying b2);
  d') maintaining the result of practicing steps a')-c') for at least one hour; and
  e') repeating steps a')-d').

Said method can provide that:
  a' b2), b3) and b4) are selected, and wherein b4) and b3) are applied sequentially in the recited order, or mixed together, in ratios selected from the group consisting of:
    a1') approximately ½ b4) and ½ b3) by volume or the equivalent by weight;
    a2') approximately ⅗ b4) and ⅖ b3) by volume or the equivalent by weight;
    a3') approximately ⅘ b4) and ⅕ b3) by volume or the equivalent by weight;
  b') applying b2) to secure said b4) and b3) in place;
  c') maintaining the result of practicing steps a')-d)' for at least one hour; and
  d') repeating steps a')-c').

Said method can provide that b3), b5) and b6) are selected and present in amounts selected from the group consisting of:
  b3), b5) and b6) are each approximately equal ⅓ parts of a total amount by volume, or the equivalent by weight,
  b5) and b6) are each approximately equal ⅖ parts with b3) being present in a lesser ⅕ part of the total by volume, or the equivalent by weight, and
  b6) is approximately ⅜, b5) approximately in a ⅖ and b3) approximately ⅙ of the total by volume, or the equivalent by weight;

said selected amounts of b3), b5) and b6) being mixed together with the result then being applied to said area of said at least one tooth that is to be smoothed, followed by selected application of b1) or b2) such that it serves to maintain contact of the mixed together b3), b5) and b6) with said area of said at least one tooth that as to be smoothed.

Said method can provide that step b) involves selection of the b1) dental cement layer to a depth of less than a millimeter, and wherein said b1) dental cement layer is applied in at least one order selected from the group consisting of:

a') before at least one selection from b3)-b6); and
b') after at least one selection from b3)-b6).
Said method can provide that the b2) composition of matter;
  adheres to teeth and serves as a barrier between teeth and gums, and the environment;
  inhibits plaque from adhering to teeth; and
  optionally dissolves and/or absorbs plaque;
wherein said method comprises selecting at least one of b4), b5) and b6), and wherein b2) and b3) are selected and mixed together to form a composition of matter that is applied to aide with securing said selected b4), b5) and/or b6) in place;
wherein the mixture of b2) and b3) composition of matter comprises:
  >0.0-4/16, nominally 1/8 adherent edible material;
  8/16-12/16, nominally 5/8 oil; and
  2/16-6/16, nominally 2/8 buffering salt.
with the amount of each component selected so that the total adds to 1.0.

A present invention method can involve selecting b1), b2) b3), b4), b5) and b6), and wherein said method comprises:
  a') applying a b1) layer of dental cement to a depth of less than one millimeter;
  b') applying b3), b4), b5) and b6), as selected from the group consisting of:
    a mixture of b3), b5) and b6);
    a mixture of b3), b4) and b5);
    a mixture of b3) and b4);
  c') applying b2);
  d') maintaining the result of practicing steps a)-c) for at least one hour; and
  e') repeating at least steps b')-d').
Said method, can provide that the b2) composition of matter;
  adheres to teeth and serves as a barrier between teeth and gums, and the environment;
  inhibits plaque from adhering to teeth; and
  optionally dissolves and/or absorbs plaque;
wherein said method comprises selecting at least one of b4), b5) and b6), and wherein b2) and b3) are selected and mixed together to form a composition of matter that is applied to aide with securing said selected b4), b5) and/or b6) in place;
wherein the mixture of b2) and b3) composition of matter comprises:
  >0.0-4/16, nominally 1/8 adherent edible material;
  8/16-12/16, nominally 5/8 oil; and
  2/16-6/16, nominally 2/8 buffering salt.
with the amount of each component selected so that the total adds to 1.0.

A present invention method can involve selecting b1), b2) b3), b4), b5) and b6), and wherein said method comprises:
  a') applying a b1) layer of dental cement to a depth of less than one millimeter;
  b') applying b3), b4), b5) and b6), as selected from the group consisting of:
    a mixture of b3), b5) and b6);
    a mixture of b3), b4) and b5);
    a mixture of b3) and b4);
  c') applying b2);
  d') maintaining the result of practicing steps a)-c) for at least one hour; and
  e') repeating steps b)-d).
Another method within the scope of the present invention provides that b3), b5) and b6) are selected and present in amounts selected from the group consisting of:
  b3), b5) and b6) are each approximately equal 1/3 parts of a total amount by volume, or the equivalent by weight,
  b5) and b6) are each approximately equal 2/5 parts with b3) being present in a lesser 1/5 part of the total by volume, or the equivalent by weight, and
  b6) is approximately 3/6, b5) approximately in a 2/6 and b3) approximately 1/6 of the total by volume, or the equivalent by weight;
said selected amounts of b3), b5) and b6) being mixed together with the result then being applied to said area of said at least one tooth that is to be smoothed, followed by selected application of b1) or b2) such that it serves to maintain contact of the mixed together b3), b5) and b6) with said area of said at least one tooth that as to be smoothed.

Another method provides that b2), b3) and b4) are selected, and wherein b4) and b3) are applied sequentially in the recited order, or mixed together, in ratios selected from the group consisting of:
  a') approximately 1/2 b4) and 1/2 b3) by volume or the equivalent by weight;
  b') approximately 3/5 b4) and 2/5 b3) by volume or the equivalent by weight;
  c') approximately 4/5 b4) and 1/5 b3) by volume or the equivalent by weight;
  d') applying b2) to secure the b4) and b3) in place;
  e') maintaining the result of practicing steps a')-d)' for at least one hour; and
  e') repeating steps b)-d).
Another method provides that step b) involves selection of the b1) dental cement layer to a depth of less than a millimeter, and wherein said b1) dental cement layer is applied in at least one order selected from the group consisting of:
  a') before at least one selection from b3)-b6); and
  b') after at least one selection from b3)-b6).

A present invention method can involve that b3), b5) and b6) are present in amounts selected from the group consisting of:
  b3), b5) and b6) are each approximately equal 1/3 parts of a total amount by volume, or the equivalent by weight,
  b5) and b6) are each approximately equal 2/5 parts with b3) being present in a lesser 1/5 part of the total by volume, or the equivalent by weight, and
  b6) is approximately 3/6, b5) approximately in a 2/6 and b3) approximately 1/6 of the total by volume, or the equivalent by weight;
wherein said selected amounts of b3), b5) and b6) are mixed together, with the result then being applied to said area of said at least one tooth that is to be smoothed, followed by selection and application of b2) such that it serves to maintain contact of the mixed together b3), b5) and b6) with said area of said at least one tooth that as to be smoothed. This can involve that b3) is a selection from the group of:
  powdered sodium bicarbonate; and
  potassium bicarbonate;
and wherein b2) is beeswax.

Said method can involve that the b2) composition of matter;
  adheres to teeth and serves as a barrier between teeth and gums, and the environment;
  inhibits plaque from adhering to teeth; and
  optionally dissolves and/or absorbs plaque;
wherein said method comprises selecting at least one of b5) and b6), and wherein b2) and b3) are selected and mixed together to form a composition of matter that is applied to aide with securing said b5) and/or b6) in place.

Said method can provide that the mixture of b2) and b3) composition of matter comprises:
>0.0-4/16, nominally 1/8 adherent edible material;
8/16-12/16, nominally 5/8 oil; and
2/16-6/16, nominally 2/8 buffering salt.
with the amount of each component selected so that the total adds to 1.0.

And, said method can provide that the buffering salt is selected from the group consisting of:
sodium bicarbonate; and
potassium bicarbonate.
(It is noted that the sodium bicarbonate can be any readily available commercial form thereof, such as that sold under the Brand Arm & Hammer, or equivalent. Similarly, any brand of potassium bicarbonate, available commercially as a salt replacement can be utilized).

Said method can provide that the adherent edible material comprises at least one selection from the group consisting of:
beeswax;
honey;
gum;
lanolin;
tallow;
carnuba;
candelilla;
soy;
ceresin;
montan;
paraffin;
ethylenic polymers;
chlorinated naphthalenes;
Fisher-Tropsch;
castor wax;
glycowax;
carnuba wax.

Said method can provide that the oil comprises at least one selection from the group consisting of an oil comprising at least one selection from the group consisting of:
castor oil;
almond oil;
cashew oil;
hazelnut oil;
macadamia oil;
pecan oil;
pistachio oil;
walnut oil;
coconut oil;
corn oil;
cottonseed oil;
canola oil;
olive oil;
palm oil;
peanut oil;
safflower oil;
seseme oil;
soybean oil;
sunflower oil;
acia oil;
blackcurrant oil;
borage oil;
evening primrose oil;
amaranth oil;
apricot oil;
argan oil;
avocado oil;
babassu oil;
ben oil from moringa oleifera;
carob oil;
coriander seed oil;
false flax oil from coriander seeds;
grape seed oil;
hemp oil;
meadowfoam seed oil;
mustard oil;
okra seed oil;
perilla seed oil;
pine seed oil;
poppyseed oil;
prune kernel oil;
pumpkinseed oil;
quinoa oil;
ramtil oil;
rice bran oil;
thistle oil;
wheat germ oil;
radish oil;
rapeseed oil;
cod oil.

Said method can provide that the composition of matter further consists of at least one selection from the group consisting of:
oils;
fragrances;
preservatives;
flavoring;
colorings;
medicinals; and
decay inhibiting materials.

Said method can provide that the composition of matter contains Beeswax and castor oil, which are the components of Oraparx® which was disclosed in the Background Section.

Said method can further involve that the composition of matter further consists of medicinals.

Said method can involve that the composition of matter further consists of at least one selection from the group:
almond flavoring;
beef flavoring;
chicken flavoring;
turkey flavoring;
lamb flavoring;
fish flavoring;
liver flavoring;
egg flavoring;
dairy flavoring;
mint flavoring;
orange flavoring.

Said method an involve that the composition of matter further consists of at least one selection from the group:
acid neutralizing material;
breath freshening material;
at least one medicinal; and
at least one decay inhibiting material.

Said method can involve that the composition of matter does not require an acid component and presents with a pH of at least 6.0.

Said method can involve that the composition of matter does not require an acid component and presents with a pH of at least 7.0.

Said method can provide that b2), and a mixture of:
b3), b5) and b6) or
b3); b4) and b5); or
b3) and b4);

is selected, and wherein the mixture of b3), b5) and b6), or b4) and b5) and b3) or b4) and b2), are contained in and applied from a single container which provides separate access to the mixture of the mixture of;
 b3), b5) and b6); or
 b4) and b5) and b3); or
 b4);
and the b2).

Said method can consisting that:
 a) at least one selection from the group consisting of:
  b4);
  b5; and
  b6);
is applied to said area of said tooth to be smoothed;
 b) a b3) composition of matter is applied to said area of said tooth to be smoothed;
 c) a b2) composition is applied is applied to said area of said tooth to be smoothed;
 d) maintaining the result of practicing steps a)-c) for at least one hour; and
 e) repeating steps b)-d).

Said method can provide that step b) involves the selections of b2) and b3) being applied in sequence or simultaneously as a mixture.

Said method can provide that step b) involves the selections of b2) and b4) being applied in sequence, or simultaneously as a mixture.

Said method can provide that step b) involves the selections of b2) and b5) being applied in sequence or simultaneously as a mixture.

Said method can provide step b) involves the selections of b2) and b6) being applied in sequence or simultaneously as a mixture.

Said method can provide that step b) comprises selecting and applying at least one of b5) and b6), and wherein said b2) is also selected and applied to aid with securing said b5) and/or b6) in place.

Said method can provide that step b) involves the selections of b1) and b4) being applied in sequence. Further, step b) can further involve selecting b3) and mixing it with b4) prior to application of said b4).

Said method can provide that step b) involves the selections of b1) and b5) being applied in sequence. Further step b) can further involve selecting b3) and mixing it with b5) prior to application of said b5).

Said method can provide that step b) involves the selections of b1) and b6) being applied in sequence. Further, step b) can further involve selecting b3) and mixing it with b6) prior to application of said b6).

Said method can provide that the step b) involves the selections of b4) and b1), applied in sequence. Further, step b) can further involve the selecting b3) and mixing it with b4) prior to application of said b4).

Said method can provide that step b) involves the selections of b5) and b1), applied in sequence. Further, step b) can further involve the selecting b3) and mixing it with b5) prior to application of said b5).

Said method can provide that step b) involves the selections of b1) and b6), applied in sequence. Further, step b) can further involve selecting b3) and mixing it with b6) prior to application of said b6).

Said method can provide that step b) involves the selections of b4) and b2), applied in sequence. Further, step b) can further involve selecting b3) and mixing it with b4) before application of said b4).

Said method can provide that step b) involves the selections, applied in sequence, of b5) and b2). Further, step b) can further involve the selecting b3) and mixing it with b5) prior to application of said b5).

Said method can involve a composition of matter comprising b3) and at least one selection from the group consisting of:
 b4);
 b5); and
 b6);
is secured within a "U" shaped element.

Said method can involve that a composition of matter comprising calcium or a calcium containing compound and said composition of matter that, when contacted by saliva provides OH⁻ ions are secured within a "U" shaped element.

Said method can involve that b2) is a wax.

A present invention method can provide that:
 a) at least one selection from the group consisting of:
  b4); and
  b5);
is applied to said area of said tooth to be smoothed, in either order;
 b) by application of a b3) composition;
 c) followed by application of a b2) composition;
 d) maintaining the result of practicing steps a)-c) for at least one hour; and
 e) repeating steps b)-d).

Said method can provide that step b) comprises selecting and applying at least one of b4), b5) and b6), then b3), and wherein said b2) is also selected and applied to aid with securing said b4) and/or b5) and/or b6) in place.

Said method can comprise the step b) involves the selections, applied in sequence, of b1) and b4).

Said method can comprise that step b) further involves the selecting b3) and mixing it with b4).

Said method can comprise that step b) involves the selections, applied in sequence, of b1) and b5).

Said method can comprise that step b) further involves the selecting b3) and mixing it with b5).

Said method can comprise that step b) involves the selections, applied in sequence, of b1) and b6).

Said method can comprise that step b) further involves the selecting b3) and mixing it with b6).

Said method can comprise that step b) involves the selections, applied in sequence, of b4) and b1).

Said method can comprise that step b) further involves the selecting b3) and mixing it with b4).

Said method can further comprise that step b) involves the selections, applied in sequence, of b5) and b1), and can further involve first selecting b3) and mixing it with b5).

Said method can comprise that step b) involves the selections, applied in sequence, of b6) and b1).

Said method can comprise that step b) further involves the selecting b3) and mixing it with b5).

Said method can comprise that step b) involves the selections, applied in sequence, of b2) and b4).

Said method can comprise that step b) further involves the selecting b3) and mixing it with b4).

Said method can comprise that step b) involves the selections, applied in sequence, of b2) and b5).

Said method can comprise that step b) further involves the selecting b3) and mixing it with b5).

Said method can comprise that step b) involves the selections, applied in sequence, of b2) and b6).

Said method can comprise that step b) further involves the selecting b3) and mixing it with b6).

Said method can comprise that step b) involves the selections, applied in sequence, of b4) and b2).

Said method can comprise that step b) further involves the selecting b3) and mixing it with b5).

Said method can comprise that step b) further involves the selecting b3) and mixing it with b4).

Said method can comprise that the step b) involves the selections, applied in sequence, of b5) and b2).

Said method can comprise that the step b) further involves the selecting b3) and mixing it with b5).

Said method can comprise that step b) involves the selections, applied in sequence, of b6) and b2).

Said method can comprise that step b) further involves the selecting b3) and mixing it with b6).

Said method can comprise that b1) is applied to a depth of a millimeter or less, followed by application of at least one selection from the group consisting of: b3), (b4), b5) and b6), followed by application of b2).

Said method can involve that a mixture of b2), b5) and b6) is applied to teeth, followed by application of a mixture of b3) and b2).

Said method an involve that a mixture of b2), b3), b4), b5) and b6) is applied to teeth.

Said method can involve that a mixture of b2) and b4) is applied to teeth, followed by application of a mixture of b3) and b2).

Said method can involve that a mixture of b2), b3) and b4) is applied to teeth.

Said method can, but does not necessarily, comprise application of a "U" shaped element over said at least one tooth, said "U" shaped element having a composition of matter present therein, and that the composition of matter causes b4) and/or b5) and/or b6) to directly contact said at least one tooth; and that a composition of matter comprising b3) is sandwiched between the "U" shaped element and the composition of matter comprising b4) and/or b5) and/or b6), to provide OH⁻ ions thereto.

Said method can comprise that b5) and b6) are selected and mixed together, and b3) and b2) are selected and mixed together, followed by applying said mixture of b5) and b6) to said area of said at least one tooth to be smoothed, followed by applying the mixture of b3) and b2) thereto.

It is to be appreciated that the commercially available product marketed for use with teeth called Lightform Band Cement, or other dental cement mentioned in the Background Section can be useful in the present invention as a means to secure a composition of matter in contact with as area of at least one tooth that is to be smoothed, where said composition is one that, when contacted by saliva provides OH⁻ ions and/or a composition of matter that comprises bio-available calcium and optional phosphate containing composition of matter and/or a powdered casein containing composition of matter and/or a powdered calcium containing composition of matter.

In addition, a composition of matter that serves as a barrier between teeth and gums and oral environment can be used for a similar purpose. Dental Waxes are an example. This can also involve a composition of matter that comprises:

>0.0-4/16, nominally 1/8 adherent edible material;
8/16-12/16, nominally 5/8 oil; and
2/16-6/16, nominally 2/8 buffering salt.

with the amount of each component selected so that the total adds to 1.0. Typical buffering salts an be selected from the group consisting of:

sodium bicarbonate; and
potassium bicarbonate;

and adherent edible material can be selected from:
beeswax;
honey;
gum;
lanolin;
tallow;
carnuba;
candelilla;
soy;
ceresin;
montan;
paraffin;
ethylenic polymers;
chlorinated naphthalenes;
Fisher-Tropsch;
castor wax;
glycowax;
carnuba wax.

Further, it is disclosed that Dental Wax disclosed in the Background Section which is available for use primarily for those who wear Braces is another is an example of an edible adherent material.

Methodology of the present invention can also provide that before, simultaneous with, or after the step b) application of bio-available calcium and optional phosphate and/or powdered calcium or casein containing composition, that there be practiced at least one selection from the group consisting of:

application of powdered casein and/or calcium, and
application of a dental cement layer to a depth of less than a millimeter either before or after.

It has been noted that maintaining contact between teeth and a composition of matter containing bio-available calcium and optional phosphate containing composition and/or powdered casein and/or calcium, can be more difficult than maintaining prolonged contact between teeth and a composition of matter comprised of:

>0.0-2/8 beeswax, nominally 1/8;
4/8-6/8 oil, nominally 5/8; and
1/8-3/8 plaque inhibiting material,
nominally 2/8;

with the amount of each component selected so that the total adds to 1.0. Application of a very thin layer of dental cement, such as that marketed under the name Lightform Brace Cement, can help in this regard. It is also noted that application of a layer of about a millimeter, or more, thereof causes formation of a cured cement that typically will not remain in place. Therefore it has been found that the depth of such an application of Dental Cement should not exceed 1 millimeter, and preferably should be far less. Applicant Welch has determined that application of a small amount of Dental Cement to an area of a tooth to be smoothed, combined with vigorously rubbing it there-onto, so that it becomes so thin that its presence can not be detected visually, but can be felt as slightly tacky by the tongue, works well. An appropriate word to describe it seems to be a "haze" of Dental Cement. Another approach to maintaining contact of Calcium or Casein based materials is to apply them, and then apply Oraparx, (ie. a material comprising 1/8 edible adhesive, 5/8 oil and 2/8 plaque inhibiting material which provides OH⁻ ions when contacted by saliva), and then optionally apply a coating of Dental Wax.

Said method can involve that the at least one tooth is present in the mouth of a human, and the optional step of surface cleaning said at least one tooth is practiced and involves surface cleaning all teeth present in said human mouth, and involves:

a') swishing hydrogen peroxide around in the mouth human's mouth for at least one minute before spitting it out;

b') preparing a toothbrush by moistening it with ethyl alcohol, followed by applying triple antibiotic ointment thereto, followed by dipping said toothbrush into Epsom Salts, followed by dipping said toothbrush into sodium bicarbonate; and then brushing said at least one human tooth with said so prepared toothbrush;

c') before spitting the results of practicing step b) out, swishing said results of practicing step b around in said human mouth for at least 15 minutes;

d') spitting out the remaining results of practicing step b) out.

Said method can involve that step b) involves MI (Trademark) Paste which is a composition of bio-available calcium and optional phosphate, and that the powdered casein Additionally, as mentioned, MI Paste is derived from Milk Casein. And the Powdered Casein can be in the form provided by Bodytech, under the name Micellar Casein, Slow Release. The manufacturer provides that said Powdered Casein contains Alanine, Arginine, Aspartic Acid, Cystein, Histadine, Isolucine, Leucine, Lysine, Methionine, Phenylanine, Proline, Serine, Threonine, Theonine, Tryptophan, Tryosine and Valine and a small amount of Potassium. It is noted that Casein can contain Protein, which comprises Amino Acids.

Said method can involve that the step c) composition of matter comprises beeswax.

Said method can involve that the step c) composition of matter comprises at least one selection from the group consisting of:
 beeswax;
 honey;
 gum;
 lanolin;
 tallow;
 carnuba;
 candelilla;
 soy;
 ceresin;
 montan;
 paraffin;
 ethylenic polymers;
 chlorinated naphthalenes;
 Fisher-Tropsch;
 castor wax;
 glycowax;
 carnuba wax; and
in which the step c) composition of matter comprises at least one selection from the group consisting of an oil comprising at least one selection from the group consisting of:
 castor oil;
 almond oil;
 cashew oil;
 hazelnut oil;
 macadamia oil;
 pecan oil;
 pistachio oil;
 walnut oil;
 coconut oil;
 corn oil;
 cottonseed oil;
 canola oil;
 olive oil;
 palm oil;
 peanut oil;
 safflower oil;
 sesame oil;
 soybean oil;
 sunflower oil;
 acia oil;
 blackcurrant oil;
 borage oil;
 evening primrose oil;
 amaranth oil;
 apricot oil;
 argan oil;
 avocado oil;
 babassu oil;
 ben oil from moringa oleifera;
 carob oil;
 coriander seed oil;
 false flax oil from coriander seeds;
 grape seed oil;
 hemp oil;
 meadowfoam seed oil;
 mustard oil;
 okra seed oil;
 perilla seed oil;
 pine seed oil;
 poppyseed oil;
 prune kernel oil;
 pumpkinseed oil;
 quinoa oil;
 ramtil oil;
 rice bran oil;
 thistle oil;
 wheat germ oil;
 radish oil;
 rapeseed oil;
 cod oil.

Said method can involve that the step c) composition of matter comprises a selection from the group consisting of:
 approximately ⅛ beeswax;
 approximately ⅛ beeswax;
 approximately ⅝ oil; and
 approximately ⅔ plaque inhibiting material; and
 (approximately ⅛ beeswax;
 approximately ⅝ oil; and
 approximately ⅔ plaque inhibiting material;
which said composition of matter being further comprises an amount of bio-available calcium and optional phosphate equal to between 1 and 100% by volume of a volume of the recited composition of matter).

It is to be appreciated that the ⅛, ⅝ and ⅔ formulation recites nominal values, and should be considered as more broadly being:
 >0.0-⅔ beeswax;
 ⅘-⅝ oil; and
 ⅛-⅘ plaque inhibiting material;
the amount of each component selected so that the total adds up to 1.0, (ie 100%).

Said method can involve that the plaque inhibiting material is selected from the group consisting of:
 sodium bicarbonate; and
 potassium bicarbonate; and
 other buffering salt.

Said method can involve that the composition of matter further comprises at least one selection from the group consisting of:
 oils;
 fragrances;
 preservatives;

flavoring;
colorings;
medicinals; and
decay inhibiting materials.
Said method can involve that the composition of matter contains beeswax and provides negative ions when warmed in a typical mamallian's mouth will cause the effect.
Said method can involve that the composition of matter:
adheres to teeth and serves as a barrier between teeth and gums, and the environment;
inhibits plaque from adhering to teeth; and
optionally dissolves and/or absorbs plague.
Said method can involve the step of applying said step c) composition of matter to said teeth via:
application from a Chap-Stick type tube of material;
application from a stick of material;
application by use of finger;
application by use of an applicator held by fingers;
application via a spray;
application by syringe; and
application via applying a strip containing said material to said teeth;
Said method can further comprise use of means for dispensing said step c) composition of matter selected from the group consisting of:
a tube comprising means for dispensing said composition of material onto teeth, said dispensing means comprising a means for causing said material to extend from said tube in a manner allowing it to be placed into contact with teeth;
a tub of composition for application via fingers or the like;
a means for spraying said material at teeth.
Said method can involve that the step c) composition of matter is fabricated by a method comprising the steps of:
a) providing an edible wax and heating it until it becomes a liquid;
b) entering a component which serves to inhibit plaque from forming on teeth and causing it to become substantially uniformly distributed therewithin;
c) cooling the result.
Said composition of matter fabrication method can involve a selection from the group consisting of:
one or more oils;
fragrances;
flavors;
preservatives;
colorings; and
medicinals;
is entered before cooling in step c.
Said method can involve said composition of material comprises, by volume, a selection from the group consisting of:
approximately:
⅛ edible adherent material, such as beeswax, (one part);
⅝ oil (five parts); and
⅖ plaque inhibiting material (two parts); and
approximately:
(⅛ beeswax;
⅝ oil; and
⅖ plaque inhibiting material, wherein said composition of matter is further comprised of an amount of bio-available calcium and optional phosphate equal to between 1 and 100% by volume of a volume of the recited composition of matter).
Said method can involve that the ⅝ oil includes medicinals.

Said method can involve repeating:
at last once a day;
at least twice a day;
at least three times a day;
at least four times a day.
Said method can involve that the composition of matter comprises at least one selection from the group consisting of:
almond flavored;
beef flavored;
chicken flavored;
turkey;
lamb flavored;
fish;
liver;
egg;
dairy flavored;
mint;
orange.
Said method can involve that the at least one tooth is from a selection form the group consisting of:
cat teeth;
dog teeth; and
human teeth.
Said method can involve that the composition of matter contains at least one selection from the group consisting of:
acid neutralizing material;
breath freshening material;
at least one medicinal; and
at least one decay inhibiting material.
Said method can involve that the composition of matter does not require an acid component and presents with a pH of at least 6.0.
Said method can involve that the steps of:
b) topically applying a bio-available calcium and optional phosphate containing composition and/or powdered casein and/or calcium, to the area on said at least one tooth that is to be smoothed; and
c) apply a composition of matter to said area of said at least one tooth that has had bio-available calcium and optional phosphate and/or powdered casein and/or calcium applied thereto, said composition of matter serving to retain said the bio-available calcium and optional phosphate and/or powdered casein and/or calcium in place;
are accomplished substantially simultaneously by providing said composition of matter in a tube or equivalent, exposing said composition of matter to bio-available calcium and optional phosphate and/or powdered casein and/or calcium as a mixture and applying the combined bio-available calcium and optional phosphate and/or powdered casein and/or calcium, and composition of matter to said at least one tooth in a single effort which substantially maintains the order of application of bio-available calcium and optional phosphate and/or powdered casein and/or calcium, and composition of matter.
Said method can also involve that the steps of:
b) topically apply bio-available calcium and optional phosphate or bio-available calcium and optional phosphate and/or powdered casein and/or calcium containing composition to the area on said at least one tooth that is to be smoothed; and
c) apply a composition of matter to said area of said at least one tooth that has had bio-available calcium and optional phosphate and/or powdered casein and/or calcium applied thereto, said composition of matter serving to retain said bio-available calcium and optional phosphate and/or powdered casein and/or calcium in place;

are accomplished substantially simultaneously by providing said composition of matter and bio-available calcium and optional phosphate and/or powdered casein and/or calcium composition in a strip, and applying the combined bio-available calcium and optional phosphate and/or powdered casein and/or calcium containing composition, and composition of matter to said at least one tooth in a single effort by applying said strip thereto, in a manner that substantially maintains the order of application of bio-available calcium and optional phosphate and/or powdered casein and/or calcium containing composition and said composition of matter.

Said method can involve that the steps of:
b) topically applying bio-available calcium and optional phosphate or bio-available calcium and optional phosphate and/or powdered casein and/or calcium containing composition to the area on said at least one tooth that is to be smoothed; and
c) apply a composition of matter to said area of said at least one tooth that has had bio-available calcium and optional phosphate or bio-available calcium and/or powdered casein and/or calcium containing composition applied thereto, said composition of matter serving to retain said bio-available calcium and optional phosphate and/or powdered casein and/or calcium containing composition in place;

are accomplished by providing said composition of matter substantially without bio-available calcium and optional phosphate and/or powdered casein and/or calcium present therein and composition of matter substantially with bio-available calcium and optional phosphate and/or powdered casein and/or calcium present therein in a tube, said composition of matter substantially with bio-available calcium and optional phosphate and/or powdered casein and/or calcium present therein being present at a selection from the group consisting of:
  at a central location therewithin; and
  surrounding said central location therewithin;
with said composition of matter substantially without bio-available calcium and optional phosphate and or powdered casein and/or calcium present therein being present at the complimentary position of:
  surrounding said central location therewithin;
  a central location therewithin;
and first causing said composition of matter containing bio-available calcium and optional phosphate and/or powdered casein and/or calcium to be applied to said at least one tooth, followed by causing said composition of matter not containing bio-available calcium and optional phosphate and/or powdered casein and/or calcium to be applied to said at least one tooth in quick succession.

Said method can involve that the steps of:
b) topically apply bio-available calcium and optional phosphate and/or powdered casein and/or calcium containing composition to the area on said at least one tooth that is to be smoothed; and
c) apply a composition of matter to said area of said at least one tooth that has had bio-available calcium and optional phosphate and/or powdered casein and/or calcium containing composition applied thereto, said composition of matter serving to retain said bio-available calcium and phosphate and/or powdered casein and/or calcium in place;

are accomplished by providing said composition of matter substantially without bio-available calcium and optional phosphate and/or powdered casein and/or calcium present therein and composition of matter substantially with bio-available calcium and optional phosphate and/or powdered casein and/or calcium present therein in a tube, said composition of matter substantially with bio-available calcium and optional phosphate and/or Powdered casein and/or calcium present therein being present at a selection from the group consisting of:
  on a first side of a diameter location therewithin; and
  on a second side of said diameter location therewithin;
with said composition of matter substantially without bio-available calcium and optional phosphate and/or powdered casein and/or calcium present therein being present at the complimentary position of:
  on said second side of said diameter location therewithin;
  on said first side of a diameter location therewithin; and
first causing said composition of matter containing bio-available calcium and optional phosphate and/or powdered casein and/or calcium to be applied to said at least one tooth, followed by causing said composition of matter not containing bio-available calcium and optional phosphate and/or powdered casein and/or calcium to be applied to said at least one tooth in quick succession.

An alternative recitation of the present invention method of smoothing teeth comprises the steps of:
a) optionally surface cleaning at least one tooth to be smoothed;
b) applying a bio-available calcium and optional phosphate and/or powdered casein and/or calcium containing composition of matter to said area of said at least one tooth;
c) applying a composition of matter to the area of said at least one tooth to which bio-available calcium and optional phosphate and/or powdered casein and/or calcium were applied to retain said bio-available calcium and optional phosphate and/or powdered casein and/or calcium in place;
d) maintaining the scenario achieved in the foregoing steps for at least half an hour.

Said alternative recited method can provide that the composition of matter that retains said bio-available calcium and optional phosphate and/or powdered casein and/or calcium in place comprises, approximately:

⅛ beeswax;

⅝ oil; and

²⁄₈ OH⁻ ion providing material;

which also optionally comprises an amount of bio-available calcium and optional phosphate and/or powdered casein and/or calcium equal to between 1 and 100% by volume of a volume of the recited composition.

A system for containing a composition of matter substantially without bio-available calcium and optional phosphate and/or powdered casein and/or calcium present therein and a composition of matter substantially with bio-available calcium and optional phosphate and/or powdered casein and/or calcium present therein, said system comprising a tube, said composition of matter with bio-available calcium and optional phosphate and/or powdered casein and/of calcium present therein being present at a selection from the group consisting of:

at a central location therewithin; and
surrounding said central location therewithin;
with said composition of matter substantially without bio-available calcium and optional phosphate and/or powdered casein and/or calcium, present therein being present at the complimentary position of:
surrounding said central location therewithin;
a central location therewithin;
such that in use a user first causes said composition of matter containing bio-available calcium and optional phosphate and/or powdered casein and/or calcium to be applied to at least one tooth, followed by causing said composition of matter not containing bio-available calcium and optional phosphate and/or powdered casein and/or calcium to be applied to said at least one tooth.

A system for containing a composition of matter substantially without bio-available calcium and optional phosphate and/or powdered casein and/or calcium present therein and a composition of matter substantially with bio-available calcium and optional phosphate and/or powdered casein and/of calcium present therein, said system comprising a tube, said composition of matter substantially with bio-available calcium and optional phosphate and/or powdered casein and/or calcium present therein being present at a selection from the group consisting of:
on a first side of a diameter location therewithin; and
on a second side of said diameter location therewithin;
with said composition of matter substantially without bio-available calcium and optional phosphate and/or powdered casein and/of calcium present therein being present at the complimentary position of:
on said second side of said diameter location therewithin;
on said first side of a diameter location therewithin; and
such that in use a user first causes said composition of matter containing bio-available calcium and optional phosphate and/or powdered casein and/or calcium to be applied to at least one tooth, followed by causing said composition of matter not containing bio-available calcium and optional phosphate and/or powdered casein and/or calcium to be applied to said at least one tooth.

It is also noted that negative limitations to Claims to avoid prior art can, but not necessarily, include that the preferred embodiment of the present invention does not involve use of enzymes, garlic, charcoal, zinc, zinc oxide, sodium percarbonate, phosphates, brushes, abrasive agents for their abrasive properties, ice, hemoglobin, oxygen, glycerin, acetic acid, citrus acid, vitis acid, (no strong acid is involved in any formulation of the present invention), peanut oil, butylene, polybutene, chewing gum, surfactants, emulsifiers, triclosan, removable backing strips, toothpastes, chewable toys, polymers, hexametaoptional, phosphate, xylitol, carbopol, staneous fluoride, sodium fluoride, calcium saltprodigiosin, magnesidin and homologs thereof, whitening agents. These, and other extraneous materials or compositions of matter and practices are identified in various cited prior art. The present invention functions by providing a barrier between teeth and an oral environment for a period of at least an hour. Any material or compositions of matter or practice not required to cause said "barrier" effect and includes a plaque inhibiting and/or reducing or other agent which reduces adherence to teeth is not required by the present invention. Such exclusions as just exemplified are simply not present in the preferred embodiment of the present invention. Neither present in the present invention method is a requirement for removal of the barrier forming agent in the present invention, although optional removal can be practiced, at some time, for aesthetic purposes.

In any present invention methodology, the method can further comprise applying a "U" shaped element over said at least one tooth, said "U" shaped element having a composition to matter present therein. The composition of matter can be formulated so that b5) and/or b6) is applied to directly contact said at least one tooth. Further, a composition of matter comprising b3) can be sandwiched between the "U" shaped element and the composition comprising b5) and/or b6) to provide OH⁻ ions thereto. The "U" shaped element can be custom made using dental Alginate.

It is noted that, as mentioned, in use application of composition of matter that serves as a barrier between teeth and gums and oral environment can be used for a similar purpose. Dental Waxes are an example. This can also involve a composition of matter that comprises:
>0.0-4/16, nominally 1/8 adherent edible material;
8/16-12/16, nominally 5/8 oil; and
2/16-6/16, nominally 2/8 buffering salt.
Likewise, prior to application of said composition of matter just recited, a composition of matter comprising:
>0.0-4/16, nominally 1/8 of b2);
8/16-12/16, nominally 5/8 oil; and
2/16-6/16, nominally 2/8 at least one selection from the group consisting of:
b3);
b4);
b5); and
b6);
can be applied.

A present invention method of smoothing teeth also consists of the steps:
a) providing at least one tooth that is to be smoothed;
b) topically applying calcium powder or calcium containing composition to an area on said at least one tooth that is to be smoothed;
c) applying a composition of matter consisting of edible adherent material, to said area of said at least one tooth that has had calcium powder or calcium containing composition applied thereto, said composition of matter serving to retain said calcium powder or calcium containing composition in place without requiring use of a backing strip;
d) maintaining the result of practicing steps a)-c) for at least one hour; and
e) repeating steps b)-d).

Said method can also consists of surface cleaning said at least one tooth prior to step a), and
in which the edible adherent material is wax, and in which the composition of matter also consists of a selection from the group consisting of:
oil;
plaque inhibiting material; and
oil and plaque inhibiting material.

Said method can involve step b) comprising powdered coral calcium.

Said method can involve step c) comprising a composition of matter comprises beeswax.

Said method can involve that the step c) composition of matter comprises at least one selection from the group consisting of:
beeswax;
honey;
gum;
lanolin;
tallow;
candelilla;
soy;

ceresin;
montan;
paraffin;
ethylenic polymers;
chlorinated naphthalenes;
castor wax; and
carnuba wax;
glycowax; and
in which the step c) composition of matter comprises at least one selection from the group consisting of an oil comprising at least one selection from the group consisting of:
castor oil;
almond oil;
cashew oil;
hazelnut oil;
macadamia oil;
pecan oil;
pistachio oil;
walnut oil;
coconut oil;
corn oil;
cottonseed oil;
canola oil;
olive oil;
palm oil;
peanut oil;
safflower oil;
seseme oil;
soybean oil;
sunflower oil;
acai oil;
blackcurrant oil;
borage oil;
evening primrose oil;
amaranth oil;
apricot oil;
argan oil;
avocado oil;
babassu oil;
ben oil from moringa oleifera;
carob oil;
coriander seed oil;
false flax oil from coriander seeds;
grape seed oil;
hemp oil;
meadowfoam seed oil;
mustard oil;
okra seed oil;
perilla seed oil;
pine seed oil;
poppyseed oil;
prune kernel oil;
pumpkinseed oil;
quinoa oil;
ramtil oil;
rice bran oil;
thistle oil;
wheat germ oil;
radish oil;
rapeseed oil; and
cod oil.

Said method can involve that the step c) composition of matter comprises a selection from the group consisting of: either:
⅛ beeswax as the edible adherent material;
⅝ oil; and
⅖ plaque inhibiting material; or
⅛ beeswax as the edible adherent material;
⅝ oil; and
⅖ plaque inhibiting material; and
that further comprises an amount of powdered calcium equal to between 1 and 100% by volume of a volume of the recited composition of matter.

Said method can involve that the plaque inhibiting material is selected from the group consisting of:
sodium bicarbonate; and
potassium bicarbonate.

Said method can involve that the composition of matter also comprises at least one selection from the group consisting of:
oils;
fragrances;
preservatives;
flavoring;
colorings; and
medicinals; and
decay inhibiting materials.

Said method can involve that the composition of matter provides negative ions.

Said method can involve that the composition of matter:
adheres to teeth and serves as a barrier between teeth and gums, and the environment;
inhibits plaque from adhering to teeth; and
optionally dissolves and/or absorbs plaque.

Said method can involve that the step of applying said step c) composition of matter to said teeth via a selection from the group consisting of:
application from a tube of material;
application from a stick of material;
application by use of finger;
application by use of an applicator held by fingers;
application via a spray;
application by syringe; and
application via use of an application brush or the like, as opposed to an toothbrush brush which serves to remove material.

Said method can also comprise use of a dispenser to dispense said step c) composition of matter selected from the group consisting of:
a tube comprising means for dispensing said composition of material onto teeth, said dispensing means comprising a means for causing said material to extend from said tube in a manner allowing it to be placed into contact with teeth;
a tub of composition for application via fingers or the like;
a sprayer.

Said method can involve that the step c) composition of matter is fabricated by a method comprising the steps of:
a') providing an edible adherent material and heating it until it becomes a liquid;
b') entering a component which serves to inhibit plaque from forming on teeth and causing it to become substantially uniformly distributed therewithin;
c') cooling the result.

Said fabrication method can involve that a selection from the group consisting of:
one or more oils;
fragrances;
flavors;
preservatives; and
colorings;
is entered before cooling in step c'.

Said method can involve that said composition of matter comprises, by volume, a selection from the group consisting of:
either:
approximately:
⅛ edible adherent material
⅝ oil; and
2/8 plaque inhibiting material; or
approximately:
⅛ edible adherent material;
⅝ oil; and
2/8 plaque inhibiting material; and
also consists of an amount of powdered calcium equal to between 1 and 100% by volume of a volume of the recited composition of matter.

Said method can involve a selection from the group consisting of repeating:
at least once a day for at least one week;
at least once a day for at least two weeks;
at least twice a day;
at least twice a day for at least two weeks;
at least once a day for more than two weeks.

Said method can involve that the composition of matter comprises at least one selection from the group consisting of:
almond flavored;
beef flavored;
chicken flavored;
turkey;
lamb flavored;
fish;
liver;
egg;
mint; and
orange.

Said method can involve that the at least one tooth is a selection from the group consisting of:
cat teeth;
dog teeth; and
human teeth.

Said method can involve that the composition of matter does not require an acid component and presents with a pH of at least 6.0.

Said method can involve that steps b) and c) are accomplished substantially simultaneously by providing said composition of matter in a tube or equivalent, exposing said composition of matter to calcium powder or calcium containing composition by dipping it thereinto, and applying the combined calcium powder and composition of matter to said at least one tooth in a single effort which substantially maintains the order of application of said calcium powder or calcium containing composition, and composition of matter.

Said method can involve that steps b) and c) are accomplished by providing said composition of matter and calcium powder or calcium containing composition in a mixture, and applying the combined calcium powder or calcium containing composition, and composition of matter to said at least one tooth in a single effort.

Said method can involve that the steps b) and c) are accomplished by providing said composition of matter substantially without calcium powder or calcium containing composition present therein and composition of matter substantially with calcium powder or calcium containing composition present therein in a tube, said composition of matter substantially without calcium powder or calcium containing composition present therein being present at a selection from the group consisting of:
at a central location therewithin; and
surrounding said central location therewithin;
with said composition of matter with calcium powder or calcium containing composition present therein being present at the complimentary position of:
surrounding said central location therewithin;
a central location therewithin;
and first causing said composition of matter containing calcium powder or calcium containing composition to be applied to said at least one tooth, followed by causing said composition of matter substantially not containing calcium powder or calcium containing composition to be applied to said at least one tooth in quick succession.

Said method can involve that the steps b) and c) are accomplished by providing said composition of matter substantially without calcium powder or calcium containing composition present therein and composition of matter substantially with calcium powder or calcium containing composition present therein in a tube, said composition of matter substantially without calcium powder or calcium containing composition present therein being present at a selection from the group consisting of:
on a first side of a diameter location therewithin; and
on a second side of said diameter location therewithin;
with said composition of matter with calcium powder or calcium containing composition present therein being present at the complimentary position of:
on said second side of said diameter location therewithin; or
on said first side of a diameter location therewithin; and
first causing said composition of matter containing calcium powder or calcium containing composition to be applied to said at least one tooth, followed by causing said composition of matter not containing calcium powder or calcium containing composition to be applied to said at least one tooth in quick succession.

Another method of smoothing teeth comprising the steps of:
a) surface cleaning at least one tooth to be smoothed;
b) applying a composition of matter to said surface cleaned at least one tooth, said composition of matter consisting of combined calcium, oil, edible adherent material and sodium and/or potassium bicarbonate, and serving to retain said calcium in place without requiring use of backing strip;
c) maintaining the scenario achieved in the foregoing steps for at least one hour.

Said method can involve that the composition of matter consists of approximately:
⅛ beeswax as the edible adherent material;
⅝ oil; and
2/8 sodium and/or potassium bicarbonate;
and also consists of an amount of powdered calcium equal to between 1 and 100% by volume, of a volume of the recited composition.

Another method of smoothing teeth consists of the steps:
a) providing at least one tooth which is to be smoothed;
b) topically applying calcium powder or calcium containing composition to an area on said at least one tooth that is to be smoothed;
c) applying a composition of matter consisting of combined wax, oil and a plaque inhibiting material, to said area of said at least one tooth that has had calcium powder or calcium containing composition applied thereto, said composition of matter serving to retain said calcium powder or calcium containing composition in place without requiring use of a backing strip, said composition of matter further comprising a source of OH⁻ ions;
d) maintaining the result of practicing steps a)-c) for at least one hour; and
e) repeating steps b)-d).

Said method can provide that the wax is beeswax, and the plaque inhibiting material is sodium and/or potassium bicarbonate.

Said method of smoothing teeth can comprise the steps:
a) providing at least one tooth that is to be smoothed;
b) topically applying calcium powder or calcium containing composition to an area on said at least one tooth that is to be smoothed;
c) applying a composition of matter consisting of edible adherent material, to said area of said at least one tooth that has had calcium powder or calcium containing composition applied thereto, said composition of matter serving to retain said calcium powder or calcium containing composition in place;
d) maintaining the result of practicing steps a)-c) for at least one hour; and
e) repeating steps b)-d).

Said method can involve that the edible adherent material also consists of oil and, optionally, a plaque inhibiting material.

Finally, it is noted to secure a date of conception therefore, that simply brushing one's teeth with a mixture of powdered calcium, (eg. coral calcium), and sodium bicarbonate, (ie. baking soda), and swishing the result around in one's mouth for about fifteen minutes or so, repeatedly, has been discovered by Applicant Welch to make his teeth in general feel more substantial. This might be evidence that OH⁻ ions provided by the sodium bicarb are catalyzing deposition of calcium to his teeth, in general.

The present invention will be better understood by reference to the Detailed Description Section of this Specification, in conjunction with the Drawings.

BRIEF DESCRIPTION OF THE DRAWINGS

FIG. 7 demonstrates application of a composition of matter via applying a form-fit "U" shaped element containing said calcium and/or casein containing composition, or another composition to teeth.

FIG. 8A demonstrates a lower tooth with rough top edge which contains a "groove", before practice of the present invention.

FIG. 8B demonstrates the lower tooth of FIG. 8A with a smoother top edge after practice of the present invention method.

DETAILED DESCRIPTION

Figure 1A:
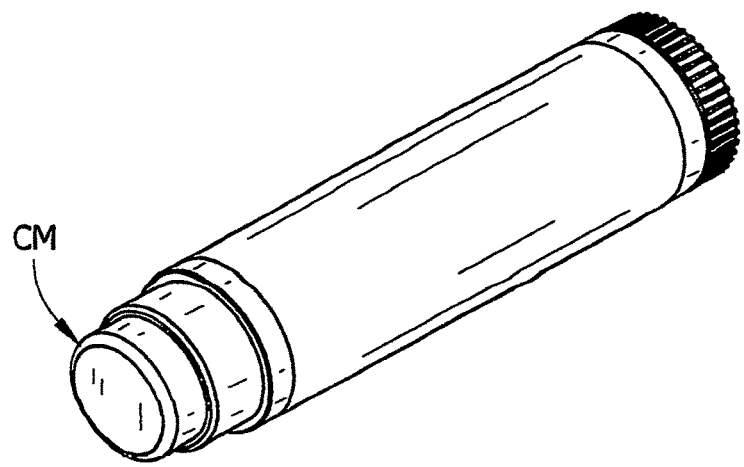
FIG. 1A shows a Chap-Stick type tubular container for composition.

Turning now to FIG. 1A, there is shown a Chap-Stick type tubular container for calcium and/or casein containing composition of matter (CM). This is a preferred embodiment.

Figure 1B:
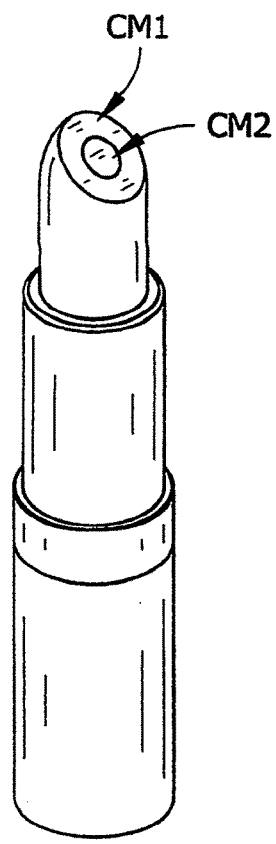
FIG. 1B shows a tubular container containing both calcium and/or casein containing and substantially not calcium and/or casein containing compositions of matter, one centrally and one surrounding said central location.

FIG. 1B shows a tubular container as in FIG. 1A, containing both calcium and/or casein containing (CM1) (CM2) and not necessarily calcium and/or casein containing (CM2) (CM1) compositions of matter, one centrally located (CM2) and one surrounding said central location (CM1). (Note, the definitely calcium and/or casein containing composition can be either centrally located, or surrounding the central location).

Figure 1C:
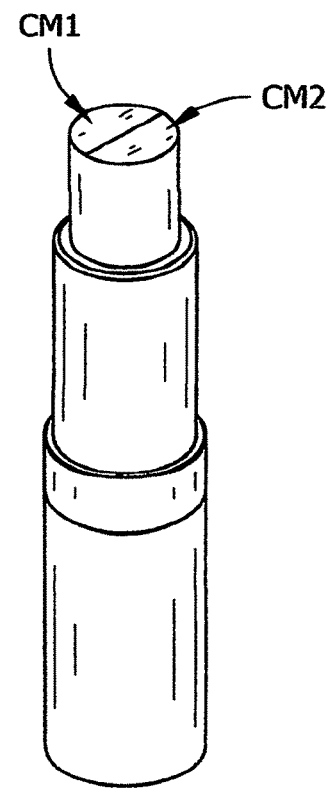
FIG. 1C shows a tubular container containing both calcium and/or casein containing and substantially not calcium and/or casein containing compositions of matter, one on one side of a diameter and one on the other side of said diameter.

FIG. 1C shows a tubular container as in FIG. 1A, containing both calcium and/or casein containing (CM1) (CM2) and not necessarily calcium and/or Casein containing (CM2) (CM1) compositions of matter, one on one side of a diameter (CM1) and one on the other side of said diameter (CM2).

Figure 2:
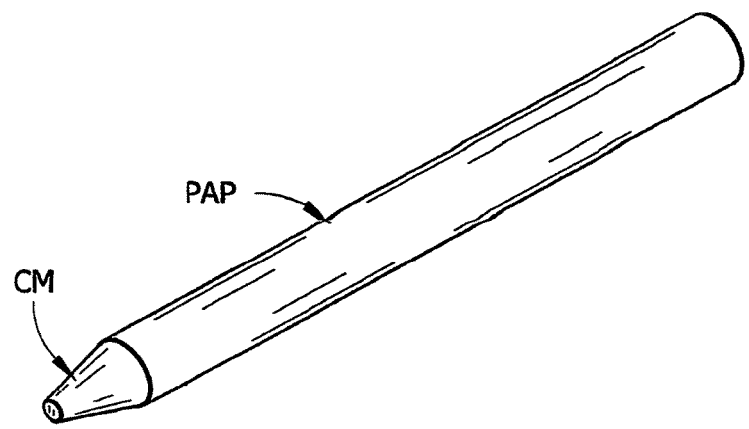
FIG. 2 shows a stick of composition material that can be applied to teeth.

FIG. 2 shows a stick of composition of matter (CM), (calcium and.or casein containing or not), that can be applied to teeth. Much like a Crayon it preferably has a surrounding paper.

Figure 3:
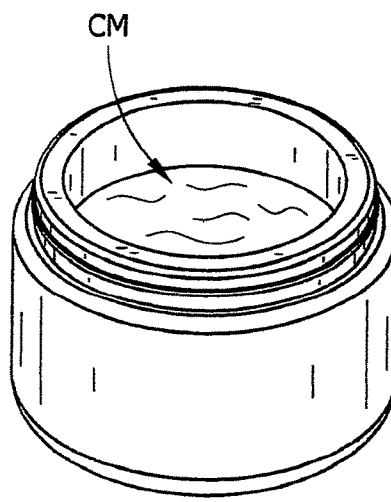
FIG. 3 demonstrates a tub of composition from which a person can apply composition by use of fingers.

FIG. 3 demonstrates a tub of composition of matter (CM) from which a user can apply composition by use of fingers.

Figure 4:
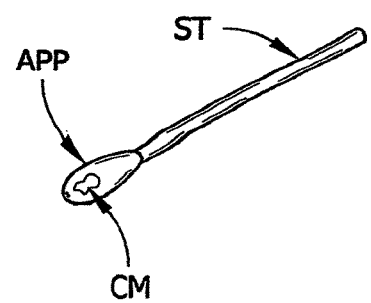
FIG. 4 demonstrates use of an applicator held by fingers to apply composition.

FIG. 4 demonstrates use of an applicator (ST) held by a user's fingers which can be used to apply composition of matter (CM).

Figure 5:
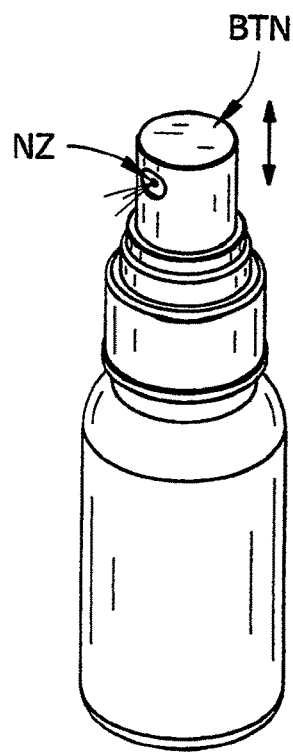
FIG. 5 demonstrates application of composition via a spray.

FIG. 5 demonstrates application of composition of matter (CM) can be via a spray container.

Figure 6:
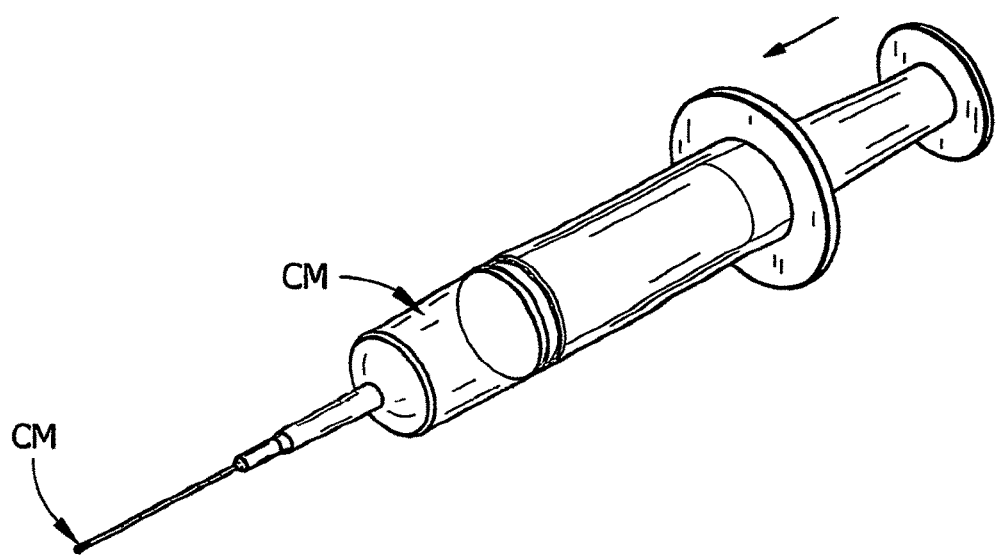
FIG. 6 demonstrates application of composition by syringe.

FIG. 6 demonstrates application of composition of matter (CM) can be by syringe.

It is noted that in the cases of FIGS. 2-6 a user will typically apply bio-available calcium and optional phosphate and/or powdered casein and/of calcium, (eg. by direct application with fingers or by brushing with a calcium containing toothpaste such as Sensodyne Pronamel, or preferably MI Paste and swishing it over teeth), to areas of teeth needing smoothing, and then apply a composition of matter, not necessarily containing calcium and/or casein, using the respective systems in said FIGS. 2-6.

When a one compartment system is utilized, it can contain a composition of matter comprising:
>0.0-4/16, nominally ⅛ of b2);
8/16-12/16, nominally ⅝ oil; and
2/16-6/16, nominally ⅖ at least one selection from the group consisting of:
b3);
b4);
b5); and
b6).

When a two compartment system is utilized, one compartment can contain a composition of matter comprising:
>0.0-4/16, nominally ⅛ of b2);
8/16-12/16, nominally ⅝ oil; and
2/16-6/16, nominally ⅖ at least one selection from the group consisting of:
b4);
b5); and
b6);

and the other a second composition of matter comprising:
>0.0-4/16, nominally 1/8 of b2);
8/16-12/16, nominally 5/8 oil; and
2/16-6/16, nominally 2/8 b3).

FIG. 7 demonstrates application of a composition of matter via applying a form-fit "U" shaped element containing said calcium and/or casein containing composition, or another composition, to teeth. The "U" shaped element directly maintains contact between the composition and teeth, and can be custom formed using dental Alginate. Note, that a try need not be for a full upper of lower set of teeth, but, for instance, can be formed to fit just one or more frontal teeth, such as shown in FIGS. 8A and 8B. It is noted that FIG. 7 can be custom fabricated by a dentist who, takes an impression of a patient's mouth, makes a plaster model therefrom, adds wax to areas corresponding to areas of a patient's teeth which are to be smoothed, followed by forming a custom-fit "U" shaped element therefrom, perhaps by a Vacu-form process. In use a patent can then apply Calcium, Casein, Oraparx etc. and then secure the result in contact with teeth with the custom-fit "U" shaped element.

FIG. 8A demonstrates a lower tooth with rough top edge which contains a "groove", before practice of the present invention.

FIG. 8B demonstrates the lower tooth of FIG. 8A with a smoother top edge after practice of the present invention method or a period of a few weeks. Extended practice of the present invention leads to progressively better results. Note, the results of FIGS. 8A and 8B have been observed and are directly the experience of Applicant Welch. He attests that his teeth have become smoother in regions of the lower edges of upper frontal teeth, and the upper edges of lower frontal teeth. Applicant Welch can only attest to the "tongue" test. His treated teeth feel much smoother when he runs his tongue over them. The way Applicant Welch stumbled onto the present invention involved brushing and swishing Sensodyne ProNamel toothpaste over the rough edged teeth. He noticed over a very long period of time that the roughness of his teeth seemed to be smoothing out. He than began using the composition Applicant Wehrli had earlier developed, as described elsewhere in the Specification, and noticed a faster pace of the roughness being smoothed. Applicant Welch cautiously reported the effect to Applicant Wehrli, but after some time reported that he knew the effect was real. He then began applying powdered Coral Calcium to the rough edges of his teeth, and noticed a much faster pace of the roughness smoothing out. Applicant Welch as been practicing the present invention primarily at night, while sleeping and has also found that results do not brush off in the morning. An improved result has been achieved using MI (Trademark), Paste in place of coral calcium and Sensodyne Pro-Enamel™. This has been augmented by use of powdered casein. Applicant Welch has recently applied said MI Paste directly to the edges of his frontal teeth and then proceeded to apply the Composition of matter. It appears to Applicant Welch that calcium has been firmly incorporated into rough edges of his teeth at an improved rate. To be completely scientifically correct, Applicant Welch can not attest that "recalcification" is a warranted term at this time, but does attest that a definite smoothing effect has occurred on rough edges of his teeth by practice of the present invention. Applicant Wehrli has suggested that the presence of "OH⁻" ions provided by her previously developed composition of matter are necessary for the effect Applicant Welch has discovered.

In any of the foregoing methodology, it is noted that the composition of matter which is applied to maintain calcium and/or casein in place can itself contain calcium such as the MI Paste containing bio-available calcium and optional phosphate.

Also, while not Claimed as such herein, it is believed that the effect Applicant Welch has discovered is the result of the recalcification of the teeth subjected to the present invention methodology. Formal research would be necessary before such a definite claim of recalcification is justified.

It is also noted that while FIGS. 1B and 1C suggest using a single tube for dispensing both Calcium containing and not necessarily Calcium containing compositions of matter, it is within the scope of the Claims to use two tubes, one for Calcium containing and one for not necessarily Calcium containing compositions of matter.

It is also noted that very recent investigation of Mr. Welch's teeth suggests that the effect described results from a rebuilding of apparent enamel from location on his teeth which still have enamel present. Observation seems to indicate that the grooves in the tops of his lower front teeth are being compensated by enamel-like material growing up and into the grooves.

Also, it has been noticed that combining Sensodyne Pro-Enamel™ with Coral Calcium prior to application to teeth seems to improve adherence properties, however, a better result has proven possible using exclusively MI Paste™, without additional Sensodyne Pro-Enamel™ and/or Coral calcium. The MI Paste™, in combination with the composition of matter that serves to hold it in place for an extended time, has proven to adhere better. The Claims are structured to allow any calcium containing material with the composition of matter that serves to hold it in place for an extended time. Where Sensodyne Pro-Enamel™ is used, the calcium includes Potassium Nitrate and Sodium Fluoride. Where MI Paste™ is used the calcium present includes phosphate.

In the foregoing, any instance of the recital of the presence of a Calcium containing composition of matter can, unless stated otherwise, also be considered to contain a provider of OH⁻ ions, such as sodium or potassium bicarbonate.

It is possible that the present invention might provide the seeds of a new approach to achieving more than smoothing rough portions of teeth. It might provide insight into a new approach to filling cavities.

Finally, it has recently been noted by Inventor Welch that brushing teeth and swishing the results around for a few minutes, using a combination of Coral Calcium and Sodium Bicarbonate in approximately equal proportions, or where the Sodium Bicarb content is reduced a bit and powdered Casein is added, results in all teeth feeling more generally more "substantial".

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:
1. A method of smoothing teeth consisting of the steps:
a) providing at least one tooth that is to be smoothed;
a') making a selection from the group of:
  practicing b) and b') and b") sequentially; or
  first mixing the components in b) and b'), and then
    practicing b and b' simultaneously, followed by b");

or
first mixing the components in b) and b') and b"), and then practicing b) and b') and b") simultaneously as a single step;
wherein b), b') and b") are:
b) applying a calcium powder or calcium containing composition to an area on said at least one tooth that is to be smoothed;
b') applying a composition of matter that, when contacted by saliva provides OH ions to said area on said at least one tooth that is to be smoothed;
b") applying an adherent material that adheres to teeth and serves as a barrier between teeth and gums and oral environment to said area of said at least one tooth said adherent material serving to retain the calcium powder or calcium containing composition and the composition of matter that, when contacted by saliva provides $OH^-$ ions in place without requiring use of a backing strip;
a") maintaining the result of practicing steps a) and a') for at least one hour; and
a'") repeating at least steps a) and a').

2. A method as in claim 1, said calcium powder or calcium containing composition comprises, in addition to calcium, phosphate, independently or as calcium phosphate; and/or casein, which comprises at least one amino acid, is also applied, in mixture with said calcium powder or calcium containing composition, or sequential thereto so that both calcium and casein are present prior to step b').

3. A method as in claim 1, wherein said calcium or calcium containing composition, and said composition of matter that when contacted by saliva provides $OH^-$ ions, are secured within a "U" shaped element that at least partially encompasses said at least one tooth.

4. A method as in claim 1, in which the composition of matter that, when contacted by saliva provides OH ions; is selected from the group of:
sodium bicarbonate; and
potassium bicarbonate; and
in which the adherent material that adheres to teeth and serves as a barrier between teeth and gums and oral environment; comprises at least one selection from the group of:
beeswax;
honey;
gum;
lanolin;
tallow;
carnuba;
candelilla;
soy;
ceresin;
montan;
paraffin;
ethylenic polymers;
chlorinated naphthalenes;
Fisher-Tropsch;
castor wax;
glycowax;
carnuba wax; and
at least one oil selected from the group of:
castor oil;
almond oil;
cashew oil;
hazelnut oil;
macadamia oil;
pecan oil;
pistachio oil;
walnut oil;
coconut oil;
corn oil;
cottonseed oil;
canola oil;
olive oil;
palm oil;
peanut oil;
safflower oil;
seseme oil;
soybean oil;
sunflower oil;
acia oil;
blackcurrant oil;
borage oil;
evening primrose oil;
amaranth oil;
apricot oil;
argan oil;
avocado oil;
babassu oil;
ben oil from moringa oleifera;
carob oil;
coriander seed oil;
false flax oil from coriander seeds;
grape seed oil;
hemp oil;
meadowfoam seed oil;
mustard oil;
okra seed oil;
perilla seed oil;
pine seed oil;
poppyseed oil;
prune kernel oil;
pumpkinseed oil;
quinoa oil;
ramtil oil;
rice bran oil;
thistle oil;
wheat germ oil;
radish oil;
rapeseed oil;
cod oil; and
at least one selection from the group of:
oils;
fragrances;
preservatives;
flavoring;
colorings;
medicinals; and
decay inhibiting materials; and
of at least one selection from the group:
almond flavoring;
beef flavoring;
chicken flavoring;
turkey flavoring;
lamb flavoring;
fish flavoring;
liver flavoring;
egg flavoring;
dairy flavoring;
mint flavoring;
orange flavoring.

5. A method as in claim 1, wherein the composition of matter that, when contacted by saliva provides OH— ions is present in a formulation presenting as:
>0.0-$4/16$, adherent edible material;
$8/16$-$12/16$ oil; and 2/16-6/16 buffering sodium or potassium bicarbonate wherein an amount of each component of the formulation is selected so that the total adds to 1.0.

* * * * *